US007361216B2

(12) United States Patent
Kangas et al.

(10) Patent No.: US 7,361,216 B2
(45) Date of Patent: *Apr. 22, 2008

(54) DENTAL COMPOSITIONS CONTAINING NANOFILLERS AND RELATED METHODS

(75) Inventors: Lani S. Kangas, Woodbury, MN (US); Hoa T. Bui, Mendota Heights, MN (US); Jason P. Thalacker, Minneapolis, MN (US); Brant U. Kolb, Afton, MN (US); Joel D. Oxman, Minneapolis, MN (US); Jacqueline C. Rolf, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/588,764

(22) Filed: Oct. 27, 2006

(65) Prior Publication Data
US 2007/0039519 A1   Feb. 22, 2007

Related U.S. Application Data

(63) Continuation of application No. 10/847,781, filed on May 17, 2004, now Pat. No. 7,156,911.

(51) Int. Cl.
A61K 6/00 (2006.01)
(52) U.S. Cl. ............... 106/35; 433/228.1; 523/115; 523/116; 523/118
(58) Field of Classification Search ............ 106/35; 523/115, 116, 118; 433/228.1
See application file for complete search history.

(56) References Cited

U.S. PATENT DOCUMENTS

| | | | |
|---|---|---|---|
| 4,070,321 A | 1/1978 | Goretta et al. |
| 4,209,434 A | 6/1980 | Wilson et al. |
| 4,259,075 A | 3/1981 | Yamauchi et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |
| 4,499,251 A | 2/1985 | Omura et al. |
| 4,503,169 A | 3/1985 | Randklev |
| 4,537,940 A | 8/1985 | Omura et al. |
| 4,539,382 A | 9/1985 | Omura et al. |
| 4,544,559 A | 10/1985 | Gil et al. |
| 4,642,126 A | 2/1987 | Zador et al. |
| 4,652,274 A | 3/1987 | Boettcher et al. |
| 4,665,217 A | 5/1987 | Reiners et al. |
| 4,695,251 A | 9/1987 | Randklev |
| 4,710,523 A | 12/1987 | Lechtken et al. |
| 4,737,593 A | 4/1988 | Ellrich et al. |
| 4,752,338 A | 6/1988 | Reiners et al. |
| 4,772,530 A | 9/1988 | Gottschalk et al. |
| 4,798,814 A | 1/1989 | Everitt et al. |
| 4,871,786 A | 10/1989 | Aasen et al. |
| 4,872,936 A | 10/1989 | Engelbrecht |
| 4,874,450 A | 10/1989 | Gottschalk |
| 4,900,697 A | 2/1990 | Akahane et al. |
| 4,954,414 A | 9/1990 | Adair et al. |
| 4,954,462 A | 9/1990 | Wood et al. |
| 5,026,902 A | 6/1991 | Fock et al. |
| 5,037,579 A | 8/1991 | Matchett |
| 5,055,372 A | 10/1991 | Shanklin et al. |
| 5,057,393 A | 10/1991 | Shanklin et al. |
| 5,063,257 A | 11/1991 | Akahane et al. |
| 5,076,844 A | 12/1991 | Fock et al. |
| 5,078,129 A | 1/1992 | Kleinberg et al. |
| 5,130,347 A | 7/1992 | Mitra |
| 5,154,762 A | 10/1992 | Mitra et al. |
| 5,179,135 A | 1/1993 | Ellis et al. |
| 5,227,413 A | 7/1993 | Mitra |
| 5,252,122 A | 10/1993 | Arnold |
| 5,332,429 A | 7/1994 | Mitra et al. |
| 5,350,782 A | 9/1994 | Sasaki et al. |
| 5,354,827 A | 10/1994 | Muller et al. |
| 5,367,002 A | 11/1994 | Huang et al. |
| 5,372,796 A | 12/1994 | Wellinghoff |
| 5,501,727 A | 3/1996 | Wang et al. |
| 5,520,725 A | 5/1996 | Kato et al. |
| 5,520,922 A | 5/1996 | Glasser et al. |
| 5,530,038 A | 6/1996 | Yamamoto et al. |
| 5,545,678 A | 8/1996 | Giencke et al. |
| 5,569,691 A | 10/1996 | Guggenberger et al. |
| 5,609,675 A | 3/1997 | Noritake et al. |

(Continued)

FOREIGN PATENT DOCUMENTS

DE    19753456 A1    6/1999

(Continued)

OTHER PUBLICATIONS

ASTM D 523-89 ( Reapproved 1994) Standard Test Method for Specular Gloss.

(Continued)

Primary Examiner—C. Melissa Koslow
(74) Attorney, Agent, or Firm—Sean J. Edman

(57) ABSTRACT

The present invention features ionomer compositions containing nanofillers. The compositions can be used in a variety of dental and orthodontic applications, for example, as adhesives, cements, restoratives, coatings and sealants.

44 Claims, No Drawings

U.S. PATENT DOCUMENTS

| | | |
|---|---|---|
| 5,670,583 A | 9/1997 | Wellinghoff |
| 5,694,701 A | 12/1997 | Huelsman et al. |
| 5,720,805 A | 2/1998 | Wellinghoff et al. |
| 5,853,792 A | 12/1998 | Zolotov et al. |
| 5,859,089 A | 1/1999 | Qian |
| 5,871,360 A | 2/1999 | Kato |
| 5,883,153 A | 3/1999 | Roberts et al. |
| 5,925,715 A | 7/1999 | Mitra |
| 5,962,550 A | 10/1999 | Akahane et al. |
| 5,965,632 A | 10/1999 | Orlowski et al. |
| 5,980,697 A | 11/1999 | Kolb et al. |
| 6,050,815 A | 4/2000 | Adam et al. |
| 6,127,449 A | 10/2000 | Bissinger et al. |
| 6,194,481 B1 | 2/2001 | Furman et al. |
| 6,214,101 B1 | 4/2001 | Nakaseko |
| 6,251,963 B1 | 6/2001 | Köhler et al. |
| 6,258,974 B1 | 7/2001 | Wellinghoff et al. |
| 6,262,142 B1 | 7/2001 | Wang et al. |
| 6,312,666 B1 | 11/2001 | Oxman et al. |
| 6,312,667 B1 | 11/2001 | Trom et al. |
| 6,353,040 B1 | 3/2002 | Subelka et al. |
| 6,376,590 B2 | 4/2002 | Kolb et al. |
| 6,383,279 B1 | 5/2002 | Eckhardt et al. |
| 6,387,981 B1 | 5/2002 | Zhang et al. |
| 6,391,286 B1 | 5/2002 | Mitra et al. |
| 6,395,801 B1 | 5/2002 | Bissinger et al. |
| 6,410,765 B1 | 6/2002 | Wellinghoff et al. |
| 6,417,244 B1 | 7/2002 | Wellinghoff et al. |
| 6,437,019 B1 | 8/2002 | Rusin et al. |
| 6,447,907 B1 | 9/2002 | Wolter et al. |
| 6,458,868 B1 | 10/2002 | Okada et al. |
| 6,472,454 B1 | 10/2002 | Qian |
| 6,540,978 B1 | 4/2003 | Margolskee |
| 6,565,873 B1 | 5/2003 | Shefer et al. |
| 6,566,413 B1 | 5/2003 | Weinmann et al. |
| 6,572,693 B1 | 6/2003 | Wu et al. |
| 6,620,405 B2 | 9/2003 | Oxman et al. |
| 6,620,861 B1 | 9/2003 | Nakatuka et al. |
| 6,624,236 B1 | 9/2003 | Bissinger et al. |
| 6,669,927 B2 | 12/2003 | Trom et al. |
| 6,693,143 B2 | 2/2004 | Pflug |
| 6,695,617 B1 | 2/2004 | Wellinghoff et al. |
| 6,696,507 B2 | 2/2004 | Subelka et al. |
| 6,696,585 B1 | 2/2004 | Wellinghoff et al. |
| 6,765,036 B2 | 7/2004 | Dede et al. |
| 6,982,288 B2 | 1/2006 | Mitra et al. |
| 7,090,721 B2 * | 8/2006 | Craig et al. .......... 106/35 |
| 7,090,722 B2 * | 8/2006 | Budd et al. .......... 106/35 |
| 7,129,281 B2 | 10/2006 | Fujiwara |
| 7,156,911 B2 * | 1/2007 | Kangas et al. .......... 106/35 |
| 2002/0013382 A1 | 1/2002 | Furman et al. |
| 2002/0177576 A1 | 11/2002 | McGregor et al. |
| 2002/0193462 A1 | 12/2002 | Angeletakis et al. |
| 2003/0055123 A1 | 3/2003 | Kawashima et al. |
| 2003/0087986 A1 | 5/2003 | Mitra |
| 2003/0166737 A1 | 9/2003 | Dede et al. |
| 2003/0166740 A1 | 9/2003 | Mitra et al. |
| 2003/0166816 A1 | 9/2003 | Bissinger et al. |
| 2003/0180414 A1 | 9/2003 | Gudas et al. |
| 2003/0181541 A1 | 9/2003 | Wu et al. |
| 2003/0195273 A1 | 10/2003 | Mitra et al. |
| 2004/0110864 A1 | 6/2004 | Hecht et al. |
| 2004/0120901 A1 | 6/2004 | Wu et al. |
| 2004/0151691 A1 | 8/2004 | Oxman et al. |
| 2004/0162375 A1 | 8/2004 | Ali et al. |
| 2004/0185013 A1 | 9/2004 | Burgio et al. |
| 2004/0197401 A1 | 10/2004 | Calton et al. |
| 2004/0206932 A1 | 10/2004 | Abuelyaman et al. |
| 2005/0203207 A1 | 9/2005 | Klettke et al. |
| 2005/0256223 A1 | 11/2005 | Kolb et al. |

FOREIGN PATENT DOCUMENTS

| | | |
|---|---|---|
| EP | 0 173 567 A2 | 3/1986 |
| EP | 0 201 031 A2 | 11/1986 |
| EP | 0 201 778 B1 | 12/1988 |
| EP | 0 373 384 B1 | 10/1992 |
| EP | 0 323 120 B1 | 3/1994 |
| EP | 0 712 622 B1 | 9/1999 |
| EP | 1 051 961 A1 | 11/2000 |
| EP | 1066813 A | 1/2001 |
| EP | 1 269 968 A1 | 1/2003 |
| GB | 1316129 A | 5/1973 |
| JP | 05 331017 A | 12/1993 |
| JP | 06 321724 A | 11/1994 |
| JP | 2000217547 | 8/2000 |
| JP | 2004 067597 A | 3/2004 |
| WO | WO 95/22956 * | 8/1995 |
| WO | 00/03688 A1 | 1/2000 |
| WO | 00/03747 A2 | 1/2000 |
| WO | 00/03747 A3 | 1/2000 |
| WO | 00/38536 A2 | 7/2000 |
| WO | 00/38536 A3 | 7/2000 |
| WO | 00/38619 A2 | 7/2000 |
| WO | 00/38619 A3 | 7/2000 |
| WO | 00/42092 A1 | 7/2000 |
| WO | 01/07444 A1 | 2/2001 |
| WO | 01/30305 A1 | 5/2001 |
| WO | 01/30306 A1 | 5/2001 |
| WO | 01/30307 A1 | 5/2001 |
| WO | 01/92271 A1 | 12/2001 |
| WO | WO 02/096464 A1 | 12/2002 |
| WO | 03/063804 | 8/2003 |
| WO | 03/063804 A1 | 8/2003 |
| WO | 03/086328 A1 | 11/2003 |
| WO | 04/043343 | 5/2004 |

OTHER PUBLICATIONS

Keast Russell S J et al: "Modifying the Bitterness of Selected Oral Pharmaceuticals with Cation and Anion Series of Salts" Database Biosis 'Online? Biosciences Infromation Service Philadelphia PA US: Jul. 2002 (Jul. 2002 XP002331214 Database accession No. PREV200200479588 Abstract & Pharmaceutical Research (new York) vol. 19 No. 7 Jul. 2002 (Jul. 2002) pp. 1019-1026 ISNN: 0724-8741.

Stamboulis et al. "Characterization of the structure of calcium alumino-silicate and calcium fluoro-alumino-silicate glasses by magic angle spinning nuclear magnetic resonance (MAS-NMR)" Journal of Non-Crystalline Solids North-Holland Physics Publishing Amsterdam NL vol. 333 No. 1 Jan. 1, 2004 pp. 01-107 XP004479772 ISSN:0022-3093 abstract.

Mathis et al., "Properties of a new glass Ionomer/Composite Resin Hybrid Restorative," Abstract No. 51, J. Dent. Res., 66:113 (1987).

Ding Ming et al., "Blocking taste receptor activation of gustducin inhibits gustatory responses to bitter compounds," Proc. Natl. Acad. Sci., USA, vol. 96:9903-9908 (Aug. 1999).

Product Information Sheet, "adenosine monophosphate" search term from the Sigma-Aldrich Catalog, datasheet [online]. Sigma Aldrich, St. Louis, Missouri, 2004 [retrieved on Jan. 7, 2005]. Retrieved from the internet: <URL:http://www.sigmaaldrich.com/catalog/search/SearchResultsPage >; 5 pgs total.

Product Information Sheet, "uridine monophosphate" search term from the Sigma-Aldrich Catalog, datasheet [online]. Sigma Aldrich, St. Louis, Missouri, 2004 [retrieved on Jan. 7, 2005]. Retrieved from the internet: <URL:http://www.sigmaaldrich.com/catalog/search/SearchResultsPage >; 2 pgs total.

Science & Technology, About Linguagen, Founder, Robert F. Margolskee; Management, Shawn M. Marcell, dated Nov. 10, 2003.

* cited by examiner

DENTAL COMPOSITIONS CONTAINING NANOFILLERS AND RELATED METHODS

CROSS REFERENCE TO RELATED APPLICATIONS

This application is a continuation of application Ser. No. 10/847,781, filed May 17, 2004, now issued as U.S. Pat. No. 7,156,911, the disclosure of which is incorporated by reference in its entirely herein.

FIELD OF THE INVENTION

The present invention relates to hardenable dental and orthodontic compositions filled with nanosized particles. More specifically, the invention relates to ionomer and resin modified ionomer compositions containing nanofillers. The compositions can be used in a variety of applications, for example, as adhesives, cements, restoratives, coatings, and sealants.

BACKGROUND

The restoration of decayed dental structures including caries, decayed dentin or decayed enamel, is often accomplished by the sequential application of a dental adhesive and then a dental material (e.g., a restorative material) to the relevant dental structures. Similar compositions are used in the bonding of orthodontic appliances (generally utilizing an orthodontic adhesive) to a dental structure. Often various pretreatment processes are used to promote the bonding of adhesives to dentin or enamel. Typically, such pretreatment steps include etching with, for example, inorganic or organic acids, followed by priming to improve the bonding between the tooth structure and the overlying adhesive.

A variety of dental and orthodontic adhesives, cements, and restoratives are currently available. Compositions including fluoroaluminosilicate glass fillers (also known as glass ionomer or "GI" compositions) are among the most widely used types of dental materials. These compositions have a broad range of applications such as filling and restoration of carious lesions; cementing of, for example, a crown, an inlay, a bridge, or an orthodontic band; lining of cavity; core construction; and pit and fissure sealing.

There are currently two major classes of glass ionomers. The first class, known as conventional glass ionomers, generally contains as main ingredients a homopolymer or copolymer of an α,β-unsaturated carboxylic acid, a fluoroaluminosilicate ("FAS") glass, water, and optionally a chelating agent such as tartaric acid. These conventional glass ionomers typically are supplied in powder/liquid formulations that are mixed just before use. The mixture undergoes self-hardening in the dark due to an ionic acid-base reaction between the acidic repeating units of the polycarboxylic acid and cations leached from the basic glass.

The second major class of glass ionomers is known as hybrid glass ionomer or resin-modified glass ionomers ("RMGI"). Like a conventional glass ionomer, an RMGI employs an FAS glass. An RMGI also contains a homopolymer or copolymer of an α,β-unsaturated carboxylic acid, an FAS glass, and water; however, the organic portion of an RMGI is different. In one type of RMGI, the polyacid is modified to replace or end-cap some of the acidic repeating units with pendent curable groups and a photoinitiator is added to provide a second cure mechanism. Acrylate or methacrylate groups are typically employed as the pendant curable group. In another type of RMGI, the composition includes a polycarboxylic acid, an acrylate or methacrylate-functional monomer or polymer, and a photoinitiator. The polyacid may optionally be modified to replace or end-cap some of the acidic repeating units with pendent curable groups. A redox or other chemical cure system may be used instead of or in addition to a photoinitiator system. RMGI compositions are usually formulated as powder/liquid or paste/paste systems, and contain water as mixed and applied. They may partially or fully harden in the dark due to the ionic reaction between the acidic repeating units of the polycarboxylic acid and cations leached from the glass, and commercial RMGI products typically also cure on exposure of the cement to light from a dental curing lamp.

There are many important benefits provided by glass ionomer compositions. For example, fluoride release from glass ionomers tends to be higher than from other classes of dental compositions such as metal oxide cements, compomer cements, or fluoridated composites, and thus glass ionomers are believed to provide enhanced cariostatic protection. Another advantage of glass ionomer materials is the very good clinical adhesion of such cements to tooth structure, thus providing highly retentive restorations. Since conventional glass ionomers do not need an external curing initiation mode, they can generally be placed in bulk as a filling material in deep restorations, without requiring layering.

One of the drawbacks of conventional glass ionomers is that these compositions are somewhat technique sensitive when mixed by hand. They are typically prepared from a powder component and a liquid component, thus requiring weighing and mixing operations prior to application. The accuracy of such operations depends in part on operator skill and competency. When mixed by hand, the powder component and the liquid component are usually mixed on paper with a spatula. The mixing operation must be carried out within a short period of time, and a skilled technique is needed in order for the material to fully exhibit the desired characteristics (i.e., the performance of the cement can depend on the mixture ratio and the manner and thoroughness of mixing). Alternatively, some of these inconveniences and technique sensitivities have been improved by utilization of powder liquid capsule dispensing systems that contain the proper proportion of the powder and liquid components. While capsules provide proper proportions of the powder and liquid components, they still require a capsule activation step to combine the two components followed by mechanical mixing in a dental triturator.

Conventional glass ionomers may also be quite brittle as evidenced by their relatively low flexural strength. Thus, restorations made from conventional glass ionomers tend to be more prone to fracture in load bearing indications. In addition, glass ionomers are often characterized by high visual opacity (i.e., cloudiness), especially when they come into contact with water at the initial stage of hardening, resulting in relatively poor aesthetics.

Cured RMGIs typically have increased strength properties (e.g., flexural strength), are less prone to mechanical fracture than conventional glass ionomers, and typically require a primer or conditioner for adequate tooth adhesion.

SUMMARY

The present invention provides stable ionomer compositions containing nanofillers that provide the compositions with improved properties over previous ionomer compositions. In one embodiment, the present invention features a hardenable dental composition comprising a polyacid; an acid-reactive filler; at least 10 percent by weight nanofiller or a combination of nanofillers each having an average particle size no more than 200 nanometers; and water. In another embodiment, the composition further comprises a polymerizable component. Generally, the polymerizable component is an ethylenically unsaturated compound, optionally with acid functionality.

The polyacid component of the composition typically comprises a polymer having a plurality of acidic repeating groups. The polymer may be substantially free of polymerizable groups, or alternatively it may comprise a plurality of polymerizable groups. In some implementations, the polyacid and the ethylenically unsaturated compound with acid functionally are the same.

The acid-reactive filler is generally selected from metal oxides, glasses, metal salts, and combinations thereof. Typically, the acid-reactive filler comprises an FAS glass. One of the advantages of the present invention is that a hardenable composition may be prepared with less acid-reactive filler than previous GI and RMGI compositions. Accordingly, in one embodiment, the composition of the invention comprises less than 50 percent by weight, in some implementations less than 30 or less than 20 weight percent, acid-reactive filler, typically an FAS glass.

In another embodiment of the invention, the acid-reactive filler comprises an oxyfluoride material, which is typically nanostructured, e.g., provided in the form of nanoparticles. Generally, the acid-reactive oxyfluoride material is non-fused and includes at least one trivalent metal (e.g., aluminum, lanthanum, etc.), oxygen, fluorine, and at least one alkaline earth metal (e.g. strontium, calcium, barium, etc.). The oxyfluoride material may be in the form of a coating on particles or nanoparticles, such as metal oxide particles (e.g., silica).

In addition to the acid-reactive filler, the composition of the invention also includes at least one nanofiller, which may be either acid reactive or non-acid reactive. Typically, the nanofiller comprises nanoparticles selected from silica; zirconia; oxides of titanium, aluminum, cerium, tin, yttrium, strontium, barium, lanthanum, zinc, ytterbium, bismuth, iron, and antimony; and combinations thereof. Often a portion of the surface of the nanofiller is silane treated or otherwise chemically treated to provide one or more desired physical properties.

In some embodiments, at least one of the nanofillers and the acid-reactive filler may be the same compound. It may also be desirable for the nanofiller component to be substantially free of fumed silica and pyrogenic fillers. In still other embodiments, the nanofiller may comprise nanoclusters, such as silica clusters, silica-zirconia clusters, and combinations thereof. The nanoclusters may contain reactive ions.

The compositions of the invention may also include one or more optional additives, such as, for example, other fillers, pyrogenic fillers, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, medicaments, indicators, dyes, pigments, wetting agents, tartaric acid, chelating agents, surfactants, buffering agents, viscosity modifiers, thixotropes, polyols, antimicrobial agents, anti-inflammatory agents, antifungal agents, stabilizers, agents for treating xerostomia, desensitizers, and combinations thereof.

The compositions of the invention may further include a photoinitiator system and/or a redox cure system.

Additionally, the compositions may be provided in the form of a multi-part system in which the various components are divided into two or more separate parts. Typically, the composition is a two-part system, such as a paste-paste composition, a paste-liquid composition, a paste-powder composition, or a powder-liquid composition.

As discussed above, one of the features of the present invention is that it provides a hardenable ionomer composition while using less acid-reactive filler than conventional glass ionomers. This facilitates the preparation of a two-part, paste-paste composition, which is generally desirable because of the ease of mixing and dispensing of such a system compared to, for example, a powder-liquid system.

Compositions according to the invention are useful in a variety of dental and orthodontic applications, including dental restoratives, dental adhesives, dental cements, cavity liners, orthodontic adhesives, dental sealants, and dental coatings. The compositions may be used to prepare a dental article by hardening to form, for example, dental mill blanks, dental crowns, dental fillings, dental prostheses, and orthodontic devices.

The ionomer compositions of the invention generally exhibit good aesthetics, low visual opacity (generally no more than about 0.50, in some implementations no more than about 0.40 or 0.30, upon hardening, as determined by the Visual Opacity (MacBeth Values) Test Method described herein), radiopacity, durability, excellent polish, polish retention (generally at least 10 percent, in some implementations at least 20 percent or at least 30 percent, as determined by the Polish Retention Test Method described herein), good wear properties, good physical properties including mechanical strengths, e.g., flexural, diametral tensile and compressive strengths, and good adhesive strength to tooth structures. Furthermore, the compositions may also provide adhesion to both dentin and enamel without the need for primers, etchants, or preconditioners. In addition, the invention provides for easy mixing and convenient dispensing options made possible by formulation of a paste-paste composition.

Other features and advantages of the present invention will be apparent from the following detailed description thereof, and from the claims.

DEFINITIONS

By "hardenable" is meant that the composition can be cured or solidified, e.g. by heating, chemical cross-linking, radiation-induced polymerization or crosslinking, or the like.

By "filler" is meant a particulate material suitable for use in the oral environment. Dental fillers generally have an average particle size of at most 100 micrometers.

By "nanofiller" is meant a filler having an average primary particle size of at most 200 nanometers. The nanofiller component may be a single nanofiller or a combination of nanofillers. Typically the nanofiller comprises non-pyrogenic nanoparticles or nanoclusters.

By "paste" is meant a soft, viscous mass of solids dispersed in a liquid.

By "acid-reactive filler" is meant a filler that chemically reacts in the presence of an acidic component.

By "oxyfluoride" is meant a material in which atoms of oxygen and fluorine are bonded to the same atom (e.g., aluminum in an aluminum oxyfluoride). Generally, at least 50% of the fluorine atoms are bonded to an atom bearing an oxygen atom in an oxyfluoride material.

By "nanostructured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" is used synonymously with "nanosized particles," and refers to particles having an average size of at most 200 nanometers. As used herein for a spherical particle, "size" refers to the diameter of the particle. As used herein for a non-spherical particle, "size" refers to the longest dimension of the particle.

By "nanocluster" is meant an association of nanoparticles drawn together by relatively weak intermolecular forces that cause them to clump together, i.e. to aggregate. Typically, nanoclusters have an average size of at most 10 micrometers.

The term "ethylenically unsaturated compounds with acid functionality" is meant to include monomers, oligomers, and polymers having ethylenic unsaturation and acid and/or acid-precursor functionality. Acid-precursor functionalities include, for example, anhydrides, acid halides, and pyrophosphates.

By "dental compositions and dental articles" is meant to include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like).

DETAILED DESCRIPTION

The present invention is directed to dental (including orthodontic) compositions, specifically ionomer compositions, e.g., glass ionomer compositions, containing a nanofiller component (i.e., one or more nanofillers). These hardenable compositions further comprise a polyacid, an acid-reactive filler, an optional polymerizable component, and water. The incorporation of one or more nanofillers into the composition provides for improved properties, including enhanced aesthetics (e.g., low visual opacity) and polish retention, as compared to previously known glass ionomer compositions.

Polymerizable Component

As mentioned above, the hardenable dental compositions of the present invention optionally include a polymerizable component. The polymerizable component can optionally be an ethylenically unsaturated compound with or without acid functionality.

The polymerizable component of the present invention can be part of a hardenable resin. These resins are generally thermosetting materials capable of being hardened to form a polymer network including, for example, acrylate-functional materials, methacrylate-functional materials, epoxy-functional materials, vinyl-functional materials, and mixtures thereof. Typically, the hardenable resin is made from one or more matrix-forming oligomer, monomer, polymer, or blend thereof.

In certain embodiments where the dental composition disclosed in the present application is a dental composite, polymerizable materials suitable for use include hardenable organic materials having sufficient strength, hydrolytic stability, and non-toxicity to render them suitable for use in the oral environment. Examples of such materials include acrylates, methacrylates, urethanes, carbamoylisocyanurates, epoxies, and mixtures and derivatives thereof.

One class of preferred hardenable materials includes materials having polymerizable components with free radically active functional groups. Examples of such materials include monomers having one or more ethylenically unsaturated groups, oligomers having one or more ethylenically unsaturated groups, polymers having one or more ethylenically unsaturated groups, and combinations thereof.

In the class of hardenable resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylete, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); copolymerizable mixtures of acrylated monomers such as those in U.S. Pat. No. 4,652,274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0 373 384 (Wagenknecht et al.), EP-0 201 031 (Reiners et al.), and EP-0 201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. Mixtures of ethylenically unsaturated compounds can be used if desired.

Polymerizable Component With Acid Functionality

When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron.

Such compounds include, for example, $\alpha,\beta$-unsaturated acidic compounds such as glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid, and the like, may be used as components in the hardenable resin system.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bis-phosphonic acids as disclosed for example, in U.S. Ser. No. 10/729,497; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

When ethylenically unsaturated compounds with acid functionality are present, the compositions of the present invention typically include at least 1% by weight, more typically at least 3% by weight, and most typically at least 5% by weight ethylenically unsaturated compounds with acid functionality, based on the total weight of the unfilled composition. Typically, compositions of the present invention include at most 50% by weight, more typically at most 40% by weight, and most typically at most 30% by weight ethylenically unsaturated compounds with acid functionality, based on the total weight of the unfilled composition.

Partial or complete hardening of the composition may occur through an acid-reactive filler/polyacid reaction (i.e. an acid/base reaction). In certain embodiments, the composition also contains a photoinitiator system that upon irradiation with actinic radiation initiates the polymerization (or hardening) of the composition. Such photopolymerizable compositions can be free radically polymerizable.

Free Radical Initiation Systems

For free radical polymerization (e.g., hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

Suitable photoinitiators (i.e., photoinitiator systems that include one or more compounds) for polymerizing free radically photopolymerizable compositions include binary and ternary systems. Typical ternary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl) borate. Preferred photosensitizers are monoketones and diketones that absorb some light within a range of about 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable ternary photoinitiator systems useful for photopolymerizing cationically polymerizable resins are described, for example, in U.S. Pat. Publication No. 2003/0166737, now U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include, for example, bis(2,4,6-trimethylbenzoyl)phenyl phosphine oxide available under the trade designation IRGACURE 819 from Ciba Specialty Chemicals, Tarrytown, N.Y.; bis(2,6-dimethoxybenzoyl)-(2,4,4-trimethylpentyl) phosphine oxide available under the trade designation CGI 403 from Ciba Specialty Chemicals; a 25:75 mixture, by weight, of bis(2,6-dimethoxybenzoyl)-2,4,4-trimethylpentyl phosphine oxide and 2-hydroxy-2-methyl-1-phenylpropan-1-one available under the trade designation IRGACURE 1700 from Ciba Specialty Chemicals; a 1:1 mixture, by weight, of bis(2,4,6-trimethylbenzoyl)phenyl phosphine oxide and 2-hydroxy-2-methyl-1-phenylpropane-1-one available under the trade designation DAROCUR 4265 from Ciba Specialty Chemicals; and ethyl 2,4,6-trimethylbenzylphenyl phosphinate available under the trade designation LUCIRIN LR8893X from BASF Corp., Charlotte, N.C.

Typically, the phosphine oxide initiator is present in the photopolymerizable composition in catalytically effective amounts, such as from 0.1% by weight to 5% by weight, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1% by weight to 5% by weight, based on the total weight of the composition. Useful amounts of other initiators are well known to those of skill in the art.

Another free-radical initiator system that can alternatively be used in the dental materials of the invention includes the class of ionic dye-counterion complex initiators including a borate anion and a complementary cationic dye. Borate salt photoinitiators are described, for example, in U.S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al.), and U.S. Pat. No. 5,057,393 (Shanklin et al.).

The hardenable resins of the present invention can include redox cure systems that include a polymerizable component (e.g., an ethylenically unsaturated polymerizable component) and redox agents that include an oxidizing agent and a reducing agent. Suitable polymerizable components and redox agents that are useful in the present invention are described in U.S. Pat. Publication No. 2003/0166740, (Mitra et al.) and U.S. Pat. Publication No. 2003/0195273, now U.S. Pat. No. 6,982,288 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include, for example, ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and combinations thereof. Preferably, the reducing agent is an amine.

Suitable oxidizing agents will also be familiar to those skilled in the art, and include, for example, persulfuric acid and salts thereof, such as sodium, potassium, ammonium, cesium, and alkyl ammonium salts. Additional oxidizing agents include, for example, peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and combinations thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the hardenable composition as described, for example, in U.S. Pat. Publication No. 2003/0195273, now U.S. Pat. No. 6,982,288 (Mitra et al.).

The reducing and oxidizing agents are present in amounts sufficient to permit an adequate free-radical reaction rate. This can be evaluated by combining all of the ingredients of the hardenable composition except for the filler, and observing whether or not a hardened mass is obtained.

Preferably, the reducing agent is present in an amount of at least 0.01% by weight, and more preferably at least 0.10% by weight, based on the total weight (including water) of the components of the hardenable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the hardenable composition.

The reducing or oxidizing agents can be microencapsulated as described, for example, in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. and at most 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

Photoinitiator compounds are preferably provided in dental compositions disclosed in the present application in an amount effective to initiate or enhance the rate of cure or hardening of the resin system. Useful photopolymerizable compositions are prepared by simply admixing, under safe light conditions, the components as described above. Suitable inert solvents may be used, if desired, when preparing this mixture. Any solvent that does not react appreciably with the components of the inventive compositions may be used. Examples of suitable solvents include, for example, acetone, dichloromethane, and acetonitrile.

Polyacid

Compositions of the present invention include at least one polyacid, which may be a non-curable or non-polymerizable polyacid, or a curable or polymerizable polyacid (e.g., a resin-modified polyacid). Typically, the polyacid is a polymer having a plurality of acidic repeating units and a plurality of polymerizable groups. In alternative embodiments, the polyacid may be substantially free of polymerizable groups. The polyacid needs not be entirely water soluble, but it should be at least sufficiently water-miscible so that it does not undergo substantial sedimentation when combined with other aqueous components. Suitable polyacids are listed in U.S. Pat. No. 4,209,434 (Wilson et al.), column 2, line 62, to column 3, line 6. The polyacid should have a molecular weight sufficient to provide good storage, handling, and mixing properties. A typical weight average molecular weight is 5,000 to 100,000, evaluated against a polystyrene standard using gel permeation chromatography.

In one embodiment, the polyacid is a curable or polymerizable resin. That is, it contains at least one ethylenically unsaturated group. Suitable ethylenically unsaturated polyacids are described in U.S. Pat. No. 4,872,936 (Engelbrecht), e.g., at columns 3 and 4, and EP 323 120 B1 (Mitra), e.g., at page 3, line 55 to page 5, line 8. Typically, the numbers of acidic groups and ethylenically unsaturated groups are adjusted to provide an appropriate balance of properties in the dental composition. Polyacids in which 10% to 70% of the acidic groups have been replaced with ethylenically unsaturated groups are preferred.

In other embodiments, the polyacid is hardenable in the presence of, for example, an acid-reactive filler and water, but does not contain ethylenically unsaturated groups. That is, it is an oligomer or polymer of an unsaturated acid. Typically, the unsaturated acid is an oxyacid (i.e., an oxygen containing acid) of carbon, sulfur, phosphorous, or boron. More typically, it is an oxyacid of carbon. Such polyacids include, for example, polyalkenoic acids such as homopolymers and copolymers of unsaturated mono-, di-, or tricarboxylic acids. Polyalkenoic acids can be prepared by the homopolymerization and copolymerization of unsaturated aliphatic carboxylic acids, e.g., acrylic acid, 2-choloracrylic acid, 3-choloracrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, and tiglic acid. Suitable monomers that can be copolymerized with the unsaturated aliphatic carboxylic acids include, for example, unsaturated aliphatic compounds such as acrylamide, acrylonitrile, vinyl chloride, allyl chloride, vinyl acetate, and 2-hydroxyethyl methacrylate. Ter- and higher polymers may be used if desired. Particularly preferred are the homopolymers and copolymers of acrylic acid. The polyalkenoic acid should be substantially free of unpolymerized monomers.

The amount of polyacid should be sufficient to react with the acid-reactive filler and to provide an ionomer composition with desirable hardening properties. Typically, the polyacid represents at least 1 wt-%, more typically at least 3 wt-%, and most typically at least 5 wt-%, based on the total weight of the unfilled composition. Typically, the polyacid represents at most 90 wt-%, more typically at most 60 wt-%, and most typically at most 30 wt-%, based on the total weight of the unfilled composition.

Acid-Reactive Fillers

Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In another embodiment, the acid-reactive filler comprises a non-fused oxyfluoride material. The oxyfluoride material may include a trivalent metal, oxygen, fluorine, and an alkaline earth metal. Preferably the trivalent metal is aluminum, lanthanum, or combinations thereof. More preferably the trivalent metal is aluminum. Preferably the alkaline earth metal is strontium, calcium, barium, or combinations thereof. In some embodiments of the present invention, the oxyfluoride material may further include silicon and/or heavy metal (e.g., zirconium, lanthanum, niobium, yttrium, or tantalum), or more specifically, oxides, fluorides and/or oxyfluorides thereof.

In some embodiments of the present invention, at least a portion of the oxyfluoride material is nanostructured. Such nanostructured materials include the oxyfluoride material in the form of, for example, nanoparticles, coatings on particles, coatings on aggregates of particles, infiltrate in a porous structure, and combinations thereof. Preferably at least 90% by weight, more preferably at least 95% by weight, and most preferably at least 98% by weight of the oxyfluoride material is nanostructured.

A description of suitable oxyfluoride materials and their use in dental compositions is provided in U.S. patent application Ser. No. 10/847,805, filed on May 17, 2004, now U.S. Pat. No. 7,090,722.

The amount of acid-reactive filler should be sufficient to provide an ionomer composition having desirable mixing and handling properties before hardening and good physical and optical properties after hardening. Generally, the reactive filler represents less than about 85% of the total weight of the composition. Typically, the acid-reactive filler represents at least 10 wt-%, and more typically at least 20 wt-%, based on the total weight of the composition. Typically, the acid-reactive filler represents at most 75 wt-%, and more typically at most 50 wt-%, based on the total weight of the composition.

Nanofillers

The composition of the invention contains one or more nanofillers which may be either acid reactive or non-acid reactive. Such nanofillers typically have an average particle size of at most 200 nanometers and more typically at most 100 nanometers. Such nanofillers typically have an average particle size of at least 2 nanometers and more typically at least 5 nanometers. Typically, the nanofiller comprises nanoparticles selected from silica; zirconia; oxides of titanium, aluminum, cerium, tin, yttrium, strontium, barium, lanthanum, zinc, ytterbium, bismuth, iron, and antimony; and combinations thereof. More typically, the nanofiller comprises nanoparticles selected from silica; zirconia; oxides of titanium; and combinations thereof. In some embodiments, the nanofiller is in the form of nanoclusters, typically at least 80 percent by weight nanoclusters. More typically the nanoclusters include silica clusters, silica-zirconia clusters, and combinations thereof. In other embodiments, the nanofiller is in the form of a combination of nanoparticles and nanoclusters. Often a portion of the surface of the nanofiller is silane treated or otherwise chemically treated to provide one or more desired physical properties.

Suitable nanofillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. patent application Ser. No. 10/847,782, filed on May 17, 2004, now U.S. Patent Publication No. 2005/0256223, and U.S. patent application Ser. No. 10/847803, filed on May 17, 2004, now U.S. Pat. No. 7,090,721.

Typically, the nanofillers of the present invention are non-pyrogenic fillers, however pyrogenic fillers can be added as optional additives to the dental compositions.

The acid-reactive, non-fused oxyfluoride materials described above that are at least partially nanostructured can be used as nanofillers in the present invention.

The amount of nanofiller should be sufficient to provide an ionomer composition having desirable mixing and handling properties before hardening and good physical and optical properties after hardening. Typically, the nanofiller represents at least 0.1 wt-%, more typically at least 10 wt-%, and most typically at least 20 wt-% or at least 15 wt-%, based on the total weight of the composition. Typically, the nanofiller represents at most 80 wt-%, more typically at most 70 wt-%, and most typically at most 60 wt-%, based on the total weight of the composition.

Other Fillers

In addition to the acid-reactive filler and the nanofiller components, the compositions of the present invention can also optionally include one or more other fillers. Such fillers may be selected from one or more of a wide variety of materials suitable for the use in dental and/or orthodontic compositions.

The other filler can be an inorganic material. It can also be a crosslinked organic material that is insoluble in the resin component of the composition, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and silica particles (e.g., submicron pyrogenic silicas such as those available under the trade designations AEROSIL, including "OX 50," "130," "150" and "200" silicas from Degussa AG, Hanau, Germany and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Examples of useful silane coupling agents are those available from Crompton Corporation, Naugatuck, Conn., as SILQUEST A-174 and SILQUEST A-1230.

For some embodiments of the present invention that include other fillers (e.g., dental restorative compositions), the compositions may include at least 1% by weight, more preferably at least 2% by weight, and most preferably at least 5% by weight other filler, based on the total weight of the composition. For such embodiments, compositions of the present invention preferably include at most 40% by weight, more preferably at most 20% by weight, and most preferably at most 15% by weight other filler, based on the total weight of the composition.

Water

The compositions of the invention contain water. The water can be distilled, deionized, or plain tap water. Typically, deionized water is used.

The amount of water should be sufficient to provide adequate handling and mixing properties and to permit the transport of ions, particularly in the filler-acid reaction. Preferably, water represents at least 2 wt-%, and more preferably at least 5 wt-%, of the total weight of ingredients used to form the composition. Preferably, water represents no greater than 90 wt-%, and more preferably no greater than 80 wt-%, of the total weight of ingredients used to form the composition.

Optional Additives

Optionally, the hardenable compositions may contain other solvents, cosolvents (e.g., alcohols) or diluents. If desired, the hardenable composition of the invention can contain additives such as indicators, dyes, pigments, inhibitors, accelerators, viscosity modifiers, wetting agents, tartaric acid, chelating agents, surfactants, buffering agents, stabilizers, and other similar ingredients that will be apparent to those skilled in the art. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of the Compositions

The hardenable dental compositions of the present invention can be prepared by combining all the various components using conventional mixing techniques. As discussed above, the compositions may be partially or fully hardened by an ionic reaction between an acid-reactive filler and a polyacid. Optionally, the compositions may contain a polymerizable component and a photoinitiator and be hardened by photoinitiation, or may be partially or fully hardened by chemical polymerization such as a redox cure system in which the composition contains a free-radical initiator system, e.g., including an oxidizing agent and a reducing agent. Alternatively, the hardenable composition may contain different initiator systems, such that the composition can be both a photopolymerizable and a chemically polymerizable composition, as well as an ionically hardenable composition.

The hardenable compositions of the invention can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, the polyacid, acid-reactive filler and water generally would not all be present in the same part, although any two of these may be grouped together in the same part along with any combination of other components. Furthermore, in a redox multi-part system, one part typically contains the oxidizing agent and another part typically contains the reducing agent. However, the reducing agent and oxidizing agent could be combined in the same part of the system if the components are kept separated, for example, through use of microencapsulation.

In one embodiment, the composition of the present invention is provided as a two-part, paste-paste system. The first part, Paste A, typically contains water, reducing agent, light cure catalyst, FAS glass, non-acid-reactive nanofillers, and radiopacifying nanofillers. Optional ingredients such as reactive nanofillers, nanocluster fillers and compatible reactive diluents and resins may be added to Paste A. The second part, Paste B, typically contains a polycarboxylic acid modified to have a small number of pendant methacrylate groups (See, e.g., U.S. Pat. Nos. 4,872,936, and 5,130,347). Paste B may also contain an acidic monomer component, nonreactive nanofillers and/or nanocluster fillers, an oxidizing agent, and a light cure catalyst. Optional ingredients for Paste A and Paste B include multifunctional methacrylate resin additives, stabilizers and colorants. This combination of ingredients in Paste A and Paste B generally provides a stable RMGI composition with primeness adhesion to dentin and enamel, radiopacity for x-ray diagnosis, and improved aesthetics. Such compositions are especially useful for bulk filling of tooth restorations by a convenient, one-step, easy mix direct restoration method.

In some embodiments, two-part dental compositions of the present invention can be provided in a dual barrel syringe having a first barrel and a second barrel, wherein the part A resides in the first barrel and the part B resides in the second barrel. In other embodiments, two-part dental compositions of the present invention can be provided in a unit-dose capsule. In some embodiments, each part of a multi-part dental system can be mixed together using a static mixer.

The components of the hardenable composition can be included in a kit, where the contents of the composition are packaged to allow for storage of the components until they are needed.

When used as a dental composition, the components of the hardenable compositions can be mixed and clinically applied using conventional techniques. A curing light is generally required for the initiation of photopolymerizable compositions. The compositions can be in the form of composites or restoratives that adhere very well to dentin and/or enamel. Optionally, a primer layer can be used on the tooth tissue on which the hardenable composition is used. The compositions, e.g., containing a FAS glass or other fluoride-releasing material, can also provide very good long-term fluoride release. Some embodiments of the invention may provide glass ionomer cements or adhesives that can be cured in bulk without the application of light or other external curing energy, do not require a pre-treatment, have improved physical properties including improved flexural strength, and have high fluoride release for cariostatic effect.

The hardenable dental compositions of the invention are particularly well adapted for use in the form of a wide variety of dental materials. They can be used in prosthodontic cements, which are typically filled compositions (preferably containing greater than about 25 wt-% filler and up to about 60 wt-% filler). They can also be used in restoratives, which include composites which are typically filled compositions (preferably containing greater than about 10 wt-% filler and up to about 85 wt-% filler) that are polymerized after being disposed adjacent to a tooth, such as filling materials. They can also be used in prostheses that are shaped and hardened for final use (e.g., as a crown, bridge, veneer, inlay, onlay, or the like), before being disposed adjacent to a tooth. Such preformed articles can be ground or otherwise formed into a custom-fitted shape by the dentist or other user. Although the hardenable dental composition can be any of a wide variety of materials preferably, the composition is not a surface pre-treatment material (e.g., etchant, primer, bonding agent). Rather, preferably, the hardenable dental composition is a restorative (e.g., composite, filling material or prosthesis), cement, sealant, coating, or orthodontic adhesive.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Particle Size Determination Test Methods

Average Particle Size by Particle Size Analyzer: Particle size (including cluster size) distribution (based on volume percent) was determined using a Coulter LS 230 Particle Size Analyzer (Coulter Corporation, Hialeah, Fla.). The Analyzer was equipped with a Polarization Intensity Differential Scanning (PIDS) software. A 300-mg sample of filler was added into a glass vial with enough MICRO-90 surfactant (Cole-Parmer, Vernon Hills, N.Y.) to wet all the filler. A 30-ml aliquot of Calgon Solution (made by thoroughly mixing 0.20 g sodium fluoride, 4.00 g sodium pyrophosphate, 40.00 g sodium hexametaphosphate, 8.00 g MICRO-90 surfactant, and 3948 ml of DI water) was added and the resulting mixture shaken for 15 minutes and sonicated by a probe sonicator (Model W-225 Sonicator, Heat Systems-Ultrasonics, Farmingdale, N.Y.) for 6 min at an output control knob setting of 9. Particle analysis was conducted using Coulter LS 230 Particle Characterization Software Version 3.01. Testing conditions were 90 seconds for Run Length, 0 seconds for Wait Length, and the test sample was added dropwise into the sample orifice until the PIDS reading was between 45% and 55%. Three sets of data per sample were averaged to obtain the average particle size.

Average Particle Size by TEM (Transmission Electron Microscopy): Samples approximately 80-nm thick were placed on 200-mesh copper grids with carbon stabilized formvar substrates (SPI Supplies, a division of Structure Probe, Inc., West Chester, Pa.). A transmission electron micrograph (TEM) was taken using a JEOL 200CX Instrument (JEOL, Ltd. of Akishima, Japan and sold by JEOL USA, Inc.) at 200 Kv. A population size of about 50-100 particles was measured and an average particle size was determined.

Adhesion to Dentin Test Method

Dentin Adhesion (DA): Dentin adhesion was measured according to the procedure described in U.S. Pat. No. 5,154,762 (Mitra et al.), but without using any pretreatment of the dentin and using a light cure exposure time of 20 seconds. Additionally, the sample was conditioned in a humidity chamber at 37° C. and 90% relative humidity for 20 minutes and then stored in deionized water for 24 hours at 37° C.

Adhesion to Enamel Test Method

Enamel Adhesion (EA): Enamel adhesion was measured according to the procedure described in U.S. Pat. No. 5,154,762 (Mitra et al.), but with the same cure time and conditioning sequence as described above for Dentin Adhesion.

Compressive Strength (CS) Test Method

Compressive strength was evaluated by first injecting a mixed paste-paste test sample into a glass tube having a 4-mm inner diameter. The ends of the glass tube were plugged with silicone plugs. The filled tubes were subjected to 0.275 megapascal (MPa) pressure for 5 minutes, irradiated with a XL 1500 curing light (3M Company) for 60 seconds, and placed in a KULZER UniXS (Kulzer, Inc., Germany) light box for 90 seconds. Five such cured samples were cut to a length of 8 mm and placed in 37° C. water for 1 day. Compressive strength was determined according to ISO Standard 7489 using an INSTRON universal tester (Instron Corp., Canton, Mass.) operated at a crosshead speed of 1 millimeter per minute (mm/min). Results were reported as the average of 5 replicates.

Diametral Tensile Strength (DTS) Test Method

Diametral tensile strength was measured using the above-described CS procedure, but using samples were cut to a length of 2 mm. Results were reported as the average of 7 replicates.

Fluoride Release (FR) Test Method

Fluoride release was evaluated in vitro by preparing mixed paste-paste test samples and placing them in a 20-mm diameter×1-mm high cylindrical mold capped with two plastic sheets clamped under moderate pressure using a C-clamp. The samples were light cured with a XL 1500 curing light (3M Company) for 60 seconds from each side, and then stored in a humidity chamber at 37° C. and 90% relative humidity for one hour. The samples were removed from the chamber and each sample immersed separately in a specimen vial containing 25 ml of deionized water in a 37° C. oven for varying periods of time. At each measurement interval, a specimen vial was removed from the oven and 10 ml of the water was measured out from the specimen vial and combined with 10 ml of TISAB II Total Ionic Strength Adjustment Buffer (Sigma Aldrich). The resulting solution was stirred and measured using a fluoride ion selective electrode to determine the cumulative micrograms of fluoride leached per gram of the test sample for the applicable measurement period, using an average of three samples. The specimen vials were replenished with fresh deionized water and returned to the oven until the next measurement period.

Visual Opacity (MacBeth Values) Test Method

Disc-shaped (1-mm thick×15-mm diameter) paste samples were cured by exposing them to illumination from a VISILUX 2 curing light (3M Co, St. Paul, Minn.) for 60 seconds on each side of the disk at a distance of 6 mm. Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Radiopacity Test Method

Disc-shaped (1-mm thick×15-mm diameter) paste test samples were cured by exposing them to illumination from an VISILUX 2 (3M Company) curing light for 60 seconds on each side of the disk at a distance of 6 mm. The cured samples were then evaluated for radiopacity as follows.

For radiopacity evaluation, the procedure used followed the ISO-test procedure 4049 (1988). Specifically, cured composite samples were exposed to radiation using a Gendex GX-770 dental X-ray (Milwaukee, Wis.) unit for 0.73 seconds at 7 milliamps and 70 kV peak voltage at a distance of about 400 millimeters. An aluminum step wedge was positioned during exposure next to the cured disk on the X-ray film. The X-ray negative was developed using an Air Techniques Peri-Pro automatic film processor (Hicksville, N.Y.). A Macbeth densitometer was used to determine the optical density of the sample disk by comparison with the optical densities of the aluminum step wedge. The reported values of optical density (i.e., radiopacity) are the average of 3 measurements.

Polish Retention Test Method

The polish retention of a hardened sample was measured by the following method. Rectangular-shaped, mixed paste-paste samples (20-mm long×9-mm wide×3-mm thick) were cured with a VISILUX 2 unit (3M Company) for 60 seconds. The light cured samples were immediately placed in a humidity chamber for 1 hour at 37° C. and 90% relative humidity. The samples were then placed in deionized water in an oven at 37° C. for 24 hours. The samples were mounted with double-sided adhesive tape (Scotch Brand Tape, Core series 2-1300, St. Paul, Minn.) to a holder and were polished according to the following series of steps that were performed sequentially as shown in Table 1. A Buehler ECOMET 4 Polisher with an AUTOMET 2 Polishing Head was used with clockwise rotation.

TABLE 1

Polishing Sequence of Steps

| Step | Procedure | (Abrasive-Grit) | Lubricant | RPM | Load (kg) per Sample | Time (Seconds) |
|---|---|---|---|---|---|---|
| 1 | Polish | SiC-320 | Water | 150 | 1.8 | 15 |
| 2 | Rinse | | Water | | | |
| 3 | Polish | SiC-600 | Water | 150 | 1.8 | 60 |
| 4 | Rinse | | Water | | | |
| 5 | Master Polish | Master Polish Abrasive | Water | 120 | 1.8 | 60 |
| 6 | Rinse | | Water | | | |

A micro-tri-gloss instrument (BYK Gardner, Columbia, Md.) was used to collect photoelectric measurements of specularly reflected light from the sample surface after polishing and after toothbrushing. The procedure described in ASTM D 523-89 (Reapproved 1994) Standard Test Method for Specular Gloss, for measurements made at 60° geometry was followed with the following modification. Initial gloss after polishing ($G_I$) was measured for initial sample. (The initial gloss value after polishing at 60° geometry was typically 80 to 86.) Final gloss after 2000 toothbrushing cycles ($G_F$) was measured. Randomly selected areas on the rectangular sample were measured for initial and final gloss. Each sample was brushed for a total of 2000 cycles with an ORAL B 40 medium Straight toothbrush (Oral B Laboratories, Belmont, Calif.) using CREST Regular Flavor (Proctor & Gamble, Cincinnati, Ohio) toothpaste. One operator brushed all of the samples using forces on the order of toothbrushing forces. Each sample was brushed with the same toothbrush. One toothbrushing cycle was a forward and a back stroke. Percent polish retention was reported as $(G_F) \times 100/(G_I)$ and was the average of 3 replications.

Three-Body Wear Test Method

The wear rate of a cured paste-paste test sample was determined by an in-vitro 3-body wear test using a Davidson Wear Tester Model 2 (ACTA, Amsterdam) unit. The Davidson Wear Tester was calibrated to ensure that the wear track was perpendicular to the wheel face. Uncured mixed paste-paste samples (constituting the first body) were loaded into a 10-mm by 4-mm slot on a 47.75-mm diameter wear wheel of the Davidson Wear Tester. The samples were cured for 60 seconds using a VISILUX 2 Curing Light (3M Company). The wear wheel, with the cured samples mounted, measured 50.80 to 53.34 mm in diameter. The cured samples on the wear wheel were machined smooth using a Carter Diamond Tool device (S-2192 SYN, Carter Diamond Tool Corp., Willoughby, Ohio) turning at 900 rpm. Water was flooded onto the wheel to control dust and to dissipate heat during the machining process. The wear wheel was kept as wet as possible during the machining.

The finial diameter of the first body wear wheel was 48.26 mm±0.254 to 0.381 mm. During testing, the first body was allowed to contact another wheel (constituting the second body) that acted as an antagonistic cusp. During contact, the two wheels were immersed in a slurry (constituting the third body) having 150 grams of ground and filtered bird seed (Wild Bird Mix, Greif Bros. Corporation, Rosemount, Minn.), 25 grams of poly(methyl methacrylate) (QuickMOUNT Powder Ingredient, Fulton Metallurgical Products Corp., Valencia, Pa.), and 275 ml of water. The two wheels were counter-rotated against each other for 166,000 cycles. Dimensional loss during these cycles was measured every 39,000 cycles by a Perthometer PRK profilometer (Feinpruef Corp., Charlotte, N.C.) along the 10-mm face of the cured and machined composite. Data were collected in a Wear Version 3 software (ACTA, Amsterdam). The data were plotted using linear regression and the wear rates for the samples were determined by calculating the slope of the lines. The wear rate for each sample was reported as a change in unit length per number of cycles (e.g., mm/cycle) and then normalized to the wear rate of a standard material, which was selected to be Z250 composite (3M Company). Thus, the reported wear resistance (average of three replications) is a dimensionless value.

Abbreviations, Descriptions, and Sources of Materials

| Abbreviation | Description and Source of Material |
|---|---|
| HEMA | 2-Hydroxyethyl methacrylate (Sigma-Aldrich, St. Louis, MO) |
| BisGMA | 2,2-Bis[4-(2-hydroxy-3-methacryloyloxy-propoxy)phenyl]propane; CAS No. 1565-94-2 |
| PEGDMA-400 | Polyethyleneglycol dimethacrylate (Sartomer 603; MW about 570; Sartomer, Exton, PA) |
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity ρ = 4.64. |
| IEM | 2-Isocyanatoethyl methacrylate (Sigma-Aldrich) |
| VBCP | Polymer made by reacting AA:ITA copolymer with sufficient IEM to convert 16 mole percent of the acid groups |

-continued

Abbreviations, Descriptions, and Sources of Materials

| Abbreviation | Description and Source of Material |
|---|---|
| | of the copolymer to pendent methacrylate groups, according to the dry polymer preparation of Example 11 of U.S. Pat. No. 5,130,347. |
| GDMA | Glycerol dimethacrylate (Rohm Tech, Inc., Malden, MA) |
| Kayamer PM-2 | Bis(methacryloxyethyl) phosphate (Nippon Kayaku, Japan) |
| Ebecryl 1830 | Polyester hexaacrylate resin (UCB-RadCure Specialties, Brussels, Belgium) |
| DMAPE | 4-Dimethylaminophenethanol (Sigma-Aldrich) |
| EDMAB | Ethyl 4-(N,N-dimethylamino)benzoate (Sigma-Aldrich) |
| BHT | Butylated hydroxytoluene (Sigma-Aldrich) |
| DPIPF6 | Diphenyliodonium hexafluorophosphate (Johnson Matthey, Alpha Aesar Division, Ward Hill, NJ) |
| CPQ | Camphorquinone (Sigma-Aldrich) |
| ATU | Allylthiourea (Sigma-Aldrich) |
| KPS | Potassium persulfate (Sigma-Aldrich) |
| $KH_2PO_4$ | Potassium dihydrogen phosphate (EM Science, Gibbstown, NJ) |
| $K_2SO_4$ | Potassium sulfate (J. T. Baker, Phillipsburg, NJ) |
| MEEAA | 2-[2-(2-methoxyethoxy)ethoxy]acetic acid (Sigma-Aldrich) |
| Zirconia Sol | Aqueous zirconia sol containing 23% solids prepared as described in U.S. Pat. No. 5,037,579 (Matchette). - Primary average particle size was determined to be 5 nm based on the Crystallite Particle Size and Crystal Form Content Test Method described in U.S. Pat. No. 6,387,981 (Zhang et al.), and average aggregated particle size was determined to be 50-60 nm based on the Photon Correlation Spectroscopy Test Method described in U.S. Pat. No. 6,387,981 (Zhang et al.) |
| Zirconia Powder | Zirconia powder, Buhler Z-W4, (Buhler LTD, Uzwil, Switzerland). Average particle size was reported by the manufacturer to be 10 nm to 40 nm. |
| SILQUEST A-174 | γ-Methacryloxypropyltrimethoxysilane used for silane treatment of fillers (Crompton Corporation, Naugatuck, CT) |
| SILQUEST A-1230 | PEG Silane used for silane treatment of fillers (Crompton Corporation) |
| AEROSIL R812S | Fumed silica filler (Degussa, Germany) |
| Filler A (FAS Glass) | Schott Glass (Product No. G 018-117; average particle size 1.0 micrometers; Schott Electronic Packaging, GmbH, Landshut, Germany). The filler was silane-treated as described for Filler FAS VI in U.S. Pat. Publication No. 2003/0166740 (Mitra et al.). |
| Filler B (FAS Glass) | "Control Glass" as described in Example 1 of U.S. Pat. No. 5,154,762 (Mitra et al.) and subsequently silane-treated as described for Filler FAS I in U.S. Pat. Publication No. 2003/0166740 (Mitra et al.). Average particle size estimated to be 3.0 micrometers, based on the Average Particle Size by Particle Size Analyzer Test Method described herein. |
| Filler C (FAS Glass) | Same as Filler B, except with additional wet milling to an average particle size estimated to be 1.0 micrometers, based on the Average Particle Size by Particle Size Analyzer Test Method described herein. |
| Filler D (FAS Glass) | A bimodal FAS filler blend of Filler B (50 weight %) and Filler C (50 weight %). |
| Filler E (Nanofiller) | Silane-treated, non-aggregated, nano-sized silica particles in the form of a dry powder were prepared according to the procedure for Filler A in U.S. Pat. Publication No. 2003/0181541 (Wu et al.). The nominal particle size of Filler E was assumed to be the same as in the starting Nalco 2329 silica sol, i.e., about 75 nanometers. |
| Filler F (Nanofiller) | Silane-treated, non-aggregated, nano-sized silica particles in the form of a dry powder were prepared according to the procedure for Filler A in U.S. Pat. Publication No. 2003/0181541 (Wu et al.), except that Nalco 2327 was used in place of Nalco 2329. The nominal particle size of Filler F was assumed to be the same as in the starting Nalco 2327 silica sol, i.e., about 20 nanometers. |
| Filler G (Nanofiller) | Silane-treated, nano-sized silica particles loosely aggregated as silica clusters were prepared in the form of a free-flowing dry powder according to the procedure for Example 1A in U.S. Pat. Publication No. 2003/0181541 (Wu et al.). The primary silica particles making up the silica clusters were assumed to be the same size as in the starting Nalco 2329 silica sol, i.e., having a nominal particle size of about 75 nanometers. |
| Filler H (Nanofiller) | Silane-treated, nano-sized silica and zirconia particles loosely aggregated as substantially amorphous clusters were prepared in the form of a dry powder according to the procedure for Filler B in U.S. Pat. Publication No. 2003/0181541 (Wu et al.). The primary silica |

-continued

| Abbreviations, Descriptions, and Sources of Materials | |
|---|---|
| Abbreviation | Description and Source of Material |
| | particles making up the silica/zirconia clusters were assumed to be the same size as in the starting Nalco 1042 silica sol, i.e., having a nominal particle size of about 20 nanometers. |
| Filler I (Prep. Ex. 1A) (Nanozirconia) | Silane-treated nano-sized zirconia filler prepared according to Preparatory Example 1A described herein. |
| Filler J | Radiopaque zirconia-silica filler prepared as described in U.S. Pat. No. 4,503,169 (Randklev). |
| Filler K (Prep. Ex. 1B) | Silane-treated nano-sized zirconia filler prepared according to Preparatory Example 1B described herein. |

Starting Materials Preparations

Preparatory Example 1A

Silane-Treated Nanozirconia

Zirconia Sol (800.0 g; 184 g zirconia) and MEEAA (72.08 g) were charged to a 1-liter round-bottom flask. The water and acid were removed via rotary evaporation to afford a powder (291.36 g) that was further dried in a forced-air oven (90° C.) to provide a dried powder (282.49 g). Deionized (DI) water (501.0 g.) was added and the powder redispersed. The resulting dispersion was charged to a 2-liter beaker followed by the addition with stirring of 1-methoxy-2-propanol (783 g; Sigma-Aldrich), SILQUEST A-174 (83.7 g) and SILQUEST A-1230 (56.3 g). The resulting mixture was stirred 30 minutes at room temperature and then separated into two quart jars and sealed. The jars were heated to 90° C. for 4.0 hours, and the contents concentrated via rotary evaporation to afford a liquid concentrate (621 g).

DI water (2400 g) and concentrated ammonia/water (80.0 g; 29% NH$_3$) were charged to a 4-liter beaker followed by the addition over about 5 minutes of the liquid concentrate to afford a white precipitate. The precipitate was recovered by vacuum filtration and washed with DI water. The resulting wet cake was dispersed in 1-methoxy-2-propanol (661 g) to afford a dispersion that contained 15.33 weight % zirconia. The silane-treated zirconia filler was designated Preparatory Example 1A (Filler I).

The above dispersion (1183 g) was combined with Resin A [HEMA (24.06 g) and PEGDMA-400 (39.59 g)] and the water and alcohol removed via rotary evaporation to afford a translucent paste that contained 80 weight % silane-treated nanozirconia filler.

Preparatory Example 1B

Silane-Treated Nanozirconia

Zirconia Powder (50 g) was charged to a quart jar with screw top. Deionized (DI) water (67.2 g) and 1-methoxy-2-propanol (99.5 g) were added and the powder dispersed. SILQUEST A-174 (10.23 g) and SILQUEST A-1230 (6.87 g) were added to the resulting dispersion while stirring. The resulting mixture was stirred 10 minutes at room temperature and then the quart jar was sealed. The jar was heated to 90° C. for 4 hours.

DI water (652 g) and concentrated ammonia/water (21.9 g; 29% NH$_3$) were charged to a 2-liter beaker followed by the addition over about 5 minutes of the liquid dispersion to afford a white precipitate. The precipitate was recovered by vacuum filtration and washed with DI water. The resulting wet cake was placed in a tray and heated to 90° C. for 4 hours. The resulting dried filter cake was crushed to afford a dry nanozirconia powder that was designated Filler K. The powder could be directly dispersed into the liquid ingredient components of the various compositions described herein.

Preparatory Example 2

Paste A Compositions

Nine first paste compositions (designated with the letter A as A1 through A9) were prepared by combining the ingredients (indicated as parts by weight) as listed in Tables 2A and 2B. Filler I (nanozirconia) was added to the compositions as a paste comprised of 80% nanozirconia in Resin A (HEMA and PEGDMA-400; see Preparatory Example 1A) and reported as a dry-weight basis in the Tables. The Resin A components are included as part of the HEMA and PEGDMA-400 components in the Tables.

TABLE 2A

Paste A Compositions

| Components (Parts by Weight) | Paste A1 | Paste A2 | Paste A3 | Paste A4 | Paste A5 |
|---|---|---|---|---|---|
| HEMA | 6.28 | 5.50 | 5.74 | 7.50 | 5.91 |
| PEGDMA-400 | 7.72 | 6.48 | 6.56 | 0 | 7.27 |
| DMAPE | 0.42 | 0.42 | 0.42 | 0.42 | 0.75 |
| CPQ | 0.10 | 0.10 | 0.10 | 0.10 | 0.05 |
| EDMAB | 0 | 0 | 0 | 0 | 0.10 |
| ATU | 0.42 | 0.42 | 0.42 | 0.42 | 0.75 |
| Filler A (FAS) | 39.72 | 40.00 | 16.39 | 0 | 40.00 |
| Filler B (FAS) | 0 | 0 | 16.39 | 41.05 | 0 |
| Filler D (FAS) | 0 | 0 | 0 | 41.05 | 0 |
| Filler F (Nano) | 16.31 | 19.30 | 36.05 | 0 | 16.28 |
| Filler G (Nano) | 0 | 0 | 8.19 | 0 | 0 |
| Filler I (Nano) | 20.57 | 20.44 | 0 | 0 | 20.57 |
| AEROSIL R812S | 0 | 0 | 0 | 0.49 | 0 |
| DI Water | 8.80 | 7.45 | 9.83 | 9.32 | 8.33 |
| Total | 100 | 100 | 100 | 100 | 100 |

TABLE 2B

Paste A Compositions

| Components (Parts by Weight) | Paste A6 | Paste A7 | Paste A8 | Paste A9 |
|---|---|---|---|---|
| HEMA | 6.28 | 6.28 | 6.28 | 6.28 |
| PEGDMA-400 | 7.73 | 7.73 | 7.73 | 7.73 |
| CPQ | 0.05 | 0.05 | 0.05 | 0.05 |

TABLE 2B-continued

Paste A Compositions

| Components (Parts by Weight) | Paste A6 | Paste A7 | Paste A8 | Paste A9 |
|---|---|---|---|---|
| EDMAB | 0.09 | 0.09 | 0.09 | 0.09 |
| Filler A (FAS) | 77 | 38.5 | 19.3 | 40.0 |
| Filler F (Nano) | 0 | 38.5 | 57.7 | 16.3 |
| Filler K (Nano) | 0 | 0 | 0 | 20.7 |
| DI Water | 8.85 | 8.85 | 8.85 | 8.85 |
| Total | 100 | 100 | 100 | 100 |

Preparatory Example 3

Paste B Compositions

Nine second paste compositions (designated with the letter B as B1 through B9) were prepared by combining the ingredients (indicated as parts by weight) as listed in Tables 3A and 3B.

TABLE 3A

Paste B Compositions

| Components (Parts by Weight) | Paste B1 | Paste B2 | Paste B3 | Paste B4 | Paste B5 | Paste B6 |
|---|---|---|---|---|---|---|
| HEMA | 20.15 | 18.92 | 18.92 | 5.06 | 23.88 | 20.07 |
| VBCP | 10.85 | 10.19 | 10.19 | 16.82 | 10.23 | 10.85 |
| AA:ITA Polyacid (80:20 wt.-%) | 0 | 0 | 0 | 6.80 | 0 | 0 |
| GDMA | 4.56 | 4.28 | 8.12 | 0 | 8.12 | 4.56 |
| BisGMA | 2.74 | 2.57 | 4.88 | 0 | 4.88 | 2.74 |
| Kayamer PM-2 | 5.17 | 4.85 | 5.00 | 0 | 0 | 5.17 |
| Ebecryl 1830 | 0.56 | 0.53 | 1.00 | 0 | 1.00 | 0.56 |
| BHT | 0.0108 | 0.01 | 0.01 | 0 | 0.01 | 0.08 |
| DPIPF6 | 0.20 | 0.20 | 0.20 | 0.20 | 0.20 | 0.15 |
| KPS | 0.50 | 0.50 | 1.80 | 1.58 | 1.80 | 1.00 |
| Filler E (Nano) | 53.50 | 56.15 | 50.00 | 0 | 50.00 | 26.53 |
| Filler J | 0 | 0 | 0 | 60.00 | 0 | 0 |
| Filler H (Nano) | 0 | 0 | 0 | 0 | 0 | 26.53 |
| AEROSIL R812S | 1.77 | 1.85 | 0 | 0 | 0 | 1.77 |
| DI Water | 0 | 0 | 0 | 9.74* | 0 | 0 |
| Total | 100 | 100 | 100 | 100 | 100 | 100 |

*Saturated salt solution containing $KH_2PO_4$ (10.72 wt. %) and $K_2SO_4$ (3.32 wt. %) in DI water.

TABLE 3B

Paste B Compositions

| Components (Parts by Weight) | Paste B7 | Paste B8 | Paste B9 |
|---|---|---|---|
| HEMA | 20.26 | 20.26 | 20.26 |
| VBCP | 10.91 | 10.91 | 10.91 |
| GDMA | 4.58 | 4.58 | 4.58 |
| BisGMA | 2.76 | 2.76 | 2.76 |
| Kayamer PM-2 | 5.20 | 5.20 | 5.20 |

TABLE 3B-continued

Paste B Compositions

| Components (Parts by Weight) | Paste B7 | Paste B8 | Paste B9 |
|---|---|---|---|
| Ebecryl 1830 | 0.56 | 0.56 | 0.56 |
| BHT | 0.08 | 0.08 | 0.08 |
| DPIPF6 | 0.15 | 0.15 | 0.15 |
| Filler E (Nano) | 0 | 26.90 | 26.90 |
| Filler J | 53.80 | 26.90 | 0 |
| Filler H (Nano) | 0 | 0 | 26.90 |
| AEROSIL R812S | 1.70 | 1.70 | 1.70 |
| Total | 100 | 100 | 100 |

Examples 1-9 and Comparative Examples 1-2

Paste A-Paste B Compositions

Hardenable compositions (Examples 1-9 and Comparative Examples 1-2) were prepared by spatulating a first paste with an equal volume of a second paste for 25 seconds. The relative parts by weight of pastes utilized and the parts by weight components in the compositions are provided in Tables 4A and 4B.

The hardenable compositions were evaluated for Compressive Strength (DS), Diametral Strength (DTS), Dentin Adhesion (DA), Enamel Adhesion (EA), Visual Opacity, Radiopacity, Fluoride Release, Polish Retention, and Three-Body Wear according to the Test Methods described herein and the results are reported in Tables 5A and 5B.

TABLE 4A

Paste A + Paste B Compositions

| Components (Parts by Weight) | Ex. 1 Paste A1 + Paste B1 (1.27:1 wt. ratio) | Ex. 2 Paste A2 + Paste B2 (1.27:1 wt. ratio) | Ex. 3 Paste A3 + Paste B3 (1.20:1 wt. ratio) | Ex. 4 Paste A3 + Paste B5 (1.20:1 wt. ratio) | Ex. 5 Paste A5 + Paste B6 (1.27:1 wt. ratio) | Comp. Ex. 1 Paste A4 + Paste B4 (1.20:1 wt. ratio) |
|---|---|---|---|---|---|---|
| HEMA | 12.39 | 11.41 | 11.73 | 13.98 | 12.15 | 6.39 |
| PEGDMA-400 | 4.32 | 3.62 | 3.58 | 3.58 | 4.07 | 0 |
| VBCP | 4.78 | 4.49 | 4.63 | 4.65 | 4.78 | 7.64 |
| AA:ITA Polyacid (80:20 wt.-%) | 0 | 0 | 0 | 0 | 0 | 3.09 |
| GDMA | 2.01 | 1.89 | 3.69 | 3.69 | 2.01 | 0 |
| BisGMA | 1.21 | 1.13 | 2.22 | 2.22 | 1.21 | 0 |
| Kayamer PM-2 | 2.28 | 2.13 | 2.27 | 0 | 2.28 | 0 |
| DMAPE | 0.23 | 0.23 | 0.23 | 0.23 | 0.42 | 0.23 |
| CPQ | 0.06 | 0.06 | 0.05 | 0.05 | 0.04 | 0.05 |
| EDMAB | 0 | 0 | 0 | 0 | 0.06 | 0 |
| ATU | 0.23 | 0.23 | 0.23 | 0.23 | 0.42 | 0.23 |
| Ebecryl 1830 | 0.25 | 0.23 | 0.45 | 0.45 | 0.25 | 0 |
| BHT | 0.005 | 0.005 | 0.005 | 0.005 | 0.04 | 0 |
| DPIPF6 | 0.09 | 0.09 | 0.09 | 0.09 | 0.07 | 0 |
| KPS | 0.22 | 0.22 | 0.82 | 0.82 | 0.44 | 0.72 |
| Filler A (FAS) | 22.22 | 22.38 | 8.94 | 8.94 | 22.38 | 0 |
| Filler B (FAS) | 0 | 0 | 8.94 | 8.94 | 0 | 0 |
| Filler D (FAS) | 0 | 0 | 0 | 0 | 0 | 44.89 |
| Filler E (Nano) | 23.57 | 24.74 | 22.73 | 22.73 | 11.69 | 0 |
| Filler F (Nano) | 9.12 | 10.80 | 19.66 | 19.66 | 9.11 | 0 |
| Filler G (Nano) | 0 | 0 | 4.47 | 4.47 | 0 | 0 |
| Filler H (Nano) | 0 | 0 | 0 | 0 | 11.69 | 0 |
| Filler I (Nano) | 11.51 | 11.44 | 0 | 0 | 11.51 | 0 |
| Filler J | 0 | 0 | 0 | 0 | 0 | 27.27 |
| AEROSIL R812S | 0.78 | 0.81 | 0 | 0 | 0.78 | 0.27 |
| DI Water | 4.92 | 4.17 | 5.36 | 5.36 | 5.36 | 4.66 |
| Total | 100 | 100 | 100 | 100 | 100 | 100* |

*Also contains $KH_2PO_4$ and $K_2SO_4$ that were present in the Paste B4 component.

TABLE 4B

Paste A + Paste B Compositions

| Components (Parts by Weight) | Comp. Ex. 2 Paste A6 + Paste B7 (1.27:1 wt. ratio) | Ex. 6 Paste A7 + Paste B8 (1.27:1 wt. ratio) | Ex. 7 Paste A7 + Paste B7 (1.27:1 wt. ratio) | Ex. 8 Paste A8 + Paste B8 (1.27:1 wt. ratio) | Ex. 9 Paste A9 + Paste B9 (1.27:1 wt. ratio) |
|---|---|---|---|---|---|
| HEMA | 12.44 | 12.44 | 12.44 | 12.44 | 12.44 |
| PEGDMA-400 | 4.32 | 4.32 | 4.32 | 4.32 | 4.32 |
| VBCP | 4.81 | 4.81 | 4.81 | 4.81 | 4.81 |
| GDMA | 2.02 | 2.02 | 2.02 | 2.02 | 2.02 |
| BisGMA | 1.22 | 1.22 | 1.22 | 1.22 | 1.22 |
| Kayamer PM-2 | 2.29 | 2.29 | 2.29 | 2.29 | 2.29 |
| CPQ | 0.03 | 0.03 | 0.03 | 0.03 | 0.03 |
| EDMAB | 0.05 | 0.05 | 0.05 | 0.05 | 0.05 |
| Ebecryl 1830 | 0.25 | 0.25 | 0.25 | 0.25 | 0.25 |
| BHT | 0.04 | 0.04 | 0.04 | 0.04 | 0.04 |
| DPIPF6 | 0.07 | 0.07 | 0.07 | 0.07 | 0.07 |
| Filler A (FAS) | 43.08 | 21.54 | 21.54 | 10.80 | 22.38 |
| Filler E (Nano) | 0 | 0 | 11.85 | 11.85 | 11.85 |
| Filler F (Nano) | 0 | 21.54 | 21.54 | 32.28 | 9.12 |
| Filler H (Nano) | 0 | 0 | 0 | 0 | 11.85 |
| Filler K (Nano) | 0 | 0 | 0 | 0 | 11.58 |
| Filler J | 23.70 | 23.70 | 11.85 | 11.85 | 0 |
| AEROSIL R812S | 0.78 | 0.78 | 0.78 | 0.78 | 0.78 |
| DI Water | 4.95 | 4.17 | 5.36 | 5.36 | 5.36 |
| Total | 100 | 100 | 100 | 100 | 100 |

TABLE 5A

Paste A + Paste B Compositions - Evaluation Results

| Test | Ex. 1<br>Paste A1 + Paste B1<br>(1.27:1 wt. ratio) | Ex. 2<br>Paste A2 + Paste B2<br>(1.27:1 wt. ratio) | Ex. 3<br>Paste A3 + Paste B3<br>(1.20:1 wt. ratio) | Ex. 4<br>Paste A3 + Paste B5<br>(1.20:1 wt. ratio) | Ex. 5<br>Paste A5 + Paste B6<br>(1.27:1 wt. ratio) | Comp. Ex. 1<br>Paste A4 + Paste B4<br>(1.20:1 wt. ratio) |
|---|---|---|---|---|---|---|
| Compressive Strength (MPa) | 290 | 312 | 272 | 266 | 289 | 211 |
| Diametral Tensile Strength (MPa) | 55 | 59 | 44 | 41 | 50 | 35 |
| Dentin Adhesion (MPa) | 6.3 | 4.0 | 7.0 | 6.0 | 5.2 | 3.2 |
| Enamel Adhesion (MPa) | 7.2 | 5.0 | 7.2 | 3.9 | 6.9 | 5.6 |
| Visual Opacity | 0.30 | 0.35 | 0.30 | 0.34 | 0.31 | 0.53 |
| Radiopacity | 1.80 | 1.74 | 0.85 | 0.85 | 2.11 | 1.75 |
| Fluoride Release (at 24 hours) (μgF/g sample) | 417 | NT* | NT | NT | 380 | NT |
| Polish Retention (%) | 22 | 33.4 | NT | NT | 30.2 | NT |
| Three-Body Wear | 4.5 | 3.02 | NT | NT | NT | NT |

*NT = Not Tested

TABLE 5B

Paste A + Paste B Compositions - Evaluation Results

| Test | Comp. Ex. 2<br>Paste A6 + Paste B7<br>(1.27:1 wt. ratio) | Ex. 6<br>Paste A7 + Paste B8<br>(1.27:1 wt. ratio) | Ex. 7<br>Paste A7 + Paste B7<br>(1.27:1 wt. ratio) | Ex. 8<br>Paste A8 + Paste B8<br>(1.27:1 wt. ratio) | Ex. 9<br>Paste A9 + Paste B9<br>(1.27:1 wt. ratio) |
|---|---|---|---|---|---|
| Nanofiller Level (wt. %) | 0 | 21.54 | 33.39 | 44.13 | 44.40 |
| Compressive Strength (MPa) | 263 | 277 | 298 | 311 | 289 |
| Visual Opacity | 0.45 | 0.43 | 0.42 | 0.27 | 0.31 |
| Radiopacity | 2.30 | 1.44 | 0.86 | 0.45 | 1.80 |
| Polish Retention (%) | 7.3 | 26.8 | 29.7 | 40.4 | 30.2 |

The results in Table 5B show that as the level of nanofiller in the compositions increases, the compressive strength and polish retention improves. The translucency (Visual Opacity) of the hardened paste-paste compositions also improves with high levels of nanofiller (e.g., Examples 8 and 9).

Comparative Example 3

VITREMER Glass Ionomer Restorative

The commercial powder-liquid VITREMER resin modified glass ionomer restorative product (3M Company) was dispensed and hand-mixed according to manufacture's directions and the resulting material was evaluated for Compressive Strength (DS), Diametral Tensile Strength (DTS), Dentin Adhesion (DA), Enamel Adhesion (EA), Visual Opacity, Radiopacity, Fluoride Release, Polish Retention, and Three-Body Wear according to the Test Methods described herein and the results are reported in Table 6.

TABLE 6

| Test | VITREMER Glass Ionomer Restorative Product |
|---|---|
| Compressive Strength (MPa) | 208 |
| Diametral Tensile Strength (MPa) | 41 |
| Dentin Adhesion (MPa) | 0 |
| Enamel Adhesion (MPa) | 2.2 |
| Visual Opacity | 0.53 |
| Radiopacity | 1.85 |
| Fluoride Release (at 24 hours) (μgF/g sample) | 326 |
| Polish Retention (%) (Initial gloss after polish was 60) | 10.4 |
| Three-Body Wear | 5.4 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A hardenable dental composition comprising:
   (a) a polyacid;
   (b) an acid-reactive filler:
   (c) at least one non-pyrogenic nanofiller; and
   (d) water;
   wherein the composition upon hardening has a visual opacity of no more than about 0.50.

2. The composition of claim 1, wherein the composition upon hardening has a visual opacity of no more than about 0.40.

3. The composition of claim 1, wherein the composition upon hardening has a visual opacity of no more than about 0.30.

4. The composition of claim 1, wherein at least one of the nanofillers and the acid-reactive filler are the same compound.

5. The composition of claim 1, wherein the composition comprises at least 15 weight percent the nanofiller or combination thereof.

6. The composition of claim 1, wherein the composition comprises at least 20 weight percent the nanofiller or combination thereof.

7. The composition of claim 1, wherein the nanofiller or combination thereof has an average particle size of at most 100 nanometers.

8. The composition of claim 1, further comprising a polymerizable component.

9. The composition of claim 8, wherein the polymerizable component comprises an ethylenically unsaturated compound.

10. The composition of claim 9, wherein the polymerizable component comprises an ethylenically unsaturated compound with acid functionality.

11. The composition of claim 10, wherein the acid functionality includes an oxygen-containing acid of carbon, sulfur, phosphorous, or boron.

12. The composition of claim 10, wherein the polyacid and the ethylenically unsaturated compound with acid functionality are the same.

13. The composition of claim 1, wherein the polyacid comprises a polymer having a plurality of acidic repeating groups but is substantially free of polymerizable groups.

14. The composition of claim 13, further comprising a polymerizable component.

15. The composition of claim 1, wherein the polyacid comprises a polymer having a plurality of acidic repeating groups and a plurality of polymerizable groups.

16. The composition of claim 15, further comprising a polymerizable component.

17. The composition of claim 1, wherein the composition is substantially free of fumed silica and pyrogenic fillers.

18. The composition of claim 1, wherein the acid-reactive filler is selected from the group consisting of metal oxides, glasses, metal salts, and combinations thereof.

19. The composition of claim 18, wherein the acid-reactive filler comprises a fluoroaluminosilicate (FAS) glass.

20. The composition of claim 19, wherein the composition comprises less than 50 weight percent FAS glass.

21. The composition of claim 19, wherein the composition comprises less than 30 weight percent FAS glass.

22. The composition of claim 19, wherein the composition comprises less than 20 weight percent FAS glass.

23. The composition of claim 1, wherein the acid-reactive filler comprises an oxyfluoride material.

24. The composition of claim 23, wherein at least 90% by weight of the oxyfluoride material is nanostructured.

25. The composition of claim 1, wherein at least one of the nanofillers is acid reactive.

26. The composition of claim 1, wherein at least one of the nanofillers is non-acid reactive.

27. The composition of claim 1, wherein the nanofiller or combination thereof comprises particles selected from the group consisting of silica; zirconia; oxides of titanium, aluminum, cerium, tin, yttrium, strontium, barium, lanthanum, zinc, ytterbium, bismuth, iron and antimony, and combinations thereof.

28. The composition of claim 1, wherein the nanofiller or combination thereof comprises particles selected from the group consisting of silica; zirconia; oxides of titanium; and combinations thereof.

29. The composition of claim 1, wherein the nanofiller comprises nanoclusters.

30. The composition of claim 1, wherein the nanofiller comprises at least 80 weight percent nanoclusters.

31. The composition of claim 29, wherein the nanoclusters are selected from the group consisting of silica clusters, silica-zirconia clusters, and combinations thereof.

32. The composition of claim 29, wherein the nanoclusters contain reactive ions.

33. The composition of claim 8, further comprising a redox cure system.

34. The composition of claim 8, further comprising a photoinitiator system.

35. The composition of claim 1, further comprising at least one additive selected from the group consisting of other fillers, pyrogenic fillers, fluoride sources, whitening agents, anticaries agents, remineralizing agents, enzymes, breath fresheners, anesthetics, clotting agents, acid neutralizers, chemotherapeutic agents, immune response modifiers, medicaments, indicators, dyes, pigments, wetting agents, tartaric acid, chelating agents, surfactants, buffering agents, viscosity modifiers, thixotropes, polyols, antimicrobial agents, anti-flammatory agents, antifungal agents, stabilizers, agents for treating xerostomia, desensitizers, and combinations thereof.

36. The composition of claim 1, wherein a portion of the surface of the nanofiller is chemically treated.

37. The composition of claim 1, wherein a portion of the surface of the nanofiller is silane treated.

38. The composition of claim 8, wherein the composition is selected from the group consisting of dental restoratives, dental adhesives, dental cements, cavity liners, orthodontic adhesives, dental sealants, and dental coatings.

39. The composition of claim 1, wherein the composition comprises a multi-part composition comprising a first part and a second part, wherein each part can independently be selected from the group consisting of a liquid, paste, gel, and powder.

40. A hardenable dental composition comprising:
    (a) a polyacid;
    (b) an acid-reactive filler;
    (c) at least one non-pyrogenic nanofiller or combination thereof; and
    (d) water;
    wherein the composition upon hardening has a polish retention of at least 10 percent.

41. The composition of claim 40, wherein the composition upon hardening has a polish retention of at least 20 percent.

42. The composition of claim 40, wherein the composition upon hardening has a polish retention of at least 30 percent.

43. A method of preparing a dental article said method comprising the steps of:
(a) providing a dental composition of claim 1, or 40; and
(b) hardening the dental composition to form the dental article.

44. The method of claim 43, wherein the dental article is selected from the group consisting of dental mill blanks, dental crowns, dental fillings, dental prostheses, and orthodontic devices.

* * * * *

UNITED STATES PATENT AND TRADEMARK OFFICE
CERTIFICATE OF CORRECTION

PATENT NO. : 7,361,216 B2
APPLICATION NO. : 11/588764
DATED : April 22, 2008
INVENTOR(S) : Lani S. Kangas It is certified that error appears in the above-identified patent and that said Letters Patent is hereby corrected as shown below:

On the Title Page, item (54), in Column 1, under (Inventors)
Line 7, after "(US)" insert -- Sumita B. Mitra, West St. Paul, MN (US) --, therefor.

On the Title Page, item (56), in Column 2, under (Continued U.S. Patents)
Line 27, delete "5,545,676    8/1996    Giencke et al." and insert
     -- 5,545,678    8/1996    Palazzotto et al. --, therefor.

On Page 2, item (56), in Column 2, under (Other Publications)
Line 3, delete "'Online?" and insert -- Online! --, therefor.
Line 3, delete "Infromation" and insert -- Information --, therefor.
Line 5, delete "PREV200200479588" and insert -- PREV200200479586 --, therefor.
Line 5, delete "new" and insert -- New --, therefor.
Line 22, delete "internet:" and insert -- Internet: --, therefor.
Line 27, delete "internet:" and insert -- Internet: --, therefor.

Column 6
Line 25, delete "tiacrylete," and insert -- tiacrylate, --, therefor.

Column 8
Line 55, delete "phenylpropan" and insert -- phenylpropane --, therefor.

Column 15
Line 67, delete "primeness" and insert -- primerless --, therefor.

Column 23
Line 27, delete "g." and insert -- g --, therefor.

Column 31
Line 4, in Claim 1, delete "filler:" and insert -- filler; --, therefor.
Line 19, in Claim 5, after "percent" delete "the".
Line 22, in Claim 6, after "percent" delete "the".

UNITED STATES PATENT AND TRADEMARK OFFICE
CERTIFICATE OF CORRECTION

PATENT NO. : 7,361,216 B2
APPLICATION NO. : 11/588764
DATED : April 22, 2008
INVENTOR(S) : Lani S. Kangas It is certified that error appears in the above-identified patent and that said Letters Patent is hereby corrected as shown below:

Column 32
Line 37, in Claim 35, delete "anti-flammatory" and insert -- anti-inflammatory --, therefor.

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,361,216 B2
APPLICATION NO. : 11/588764
DATED : April 22, 2008
INVENTOR(S) : Lani S. Kangas It is certified that error appears in the above-identified patent and that said Letters Patent is hereby corrected as shown below:

On the Title Page, item (75), in Column 1, under (Inventors)
Line 7, after "(US)" insert -- Sumita B. Mitra, West St. Paul, MN (US) --, therefor.

On the Title Page, item (56), in Column 2, under (Continued U.S. Patents)
Line 27, delete "5,545,676      8/1996      Giencke et al." and insert
  -- 5,545,678      8/1996      Palazzotto et al. --, therefor.

On Page 2, item (56), in Column 2, under (Other Publications)
Line 3, delete "'Online?" and insert -- Online! --, therefor.
Line 3, delete "Infromation" and insert -- Information --, therefor.
Line 5, delete "PREV200200479588" and insert -- PREV200200479586 --, therefor.
Line 5, delete "new" and insert -- New --, therefor.
Line 22, delete "internet:" and insert -- Internet: --, therefor.
Line 27, delete "internet:" and insert -- Internet: --, therefor.

Column 6
Line 25, delete "tiacrylete," and insert -- tiacrylate, --, therefor.

Column 8
Line 55, delete "phenylpropan" and insert -- phenylpropane --, therefor.

Column 15
Line 67, delete "primeness" and insert -- primerless --, therefor.

Column 23
Line 27, delete "g." and insert -- g --, therefor.

Column 31
Line 4, in Claim 1, delete "filler:" and insert -- filler; --, therefor.
Line 19, in Claim 5, after "percent" delete "the".
Line 22, in Claim 6, after "percent" delete "the".

UNITED STATES PATENT AND TRADEMARK OFFICE
CERTIFICATE OF CORRECTION

PATENT NO. : 7,361,216 B2
APPLICATION NO. : 11/588764
DATED : April 22, 2008
INVENTOR(S) : Lani S. Kangas It is certified that error appears in the above-identified patent and that said Letters Patent is hereby corrected as shown below:

Column 32
Line 37, in Claim 35, delete "anti-flammatory" and insert -- anti-inflammatory --, therefor.

This certificate supersedes the Certificate of Correction issued February 17, 2009.

Signed and Sealed this

Seventeenth Day of March, 2009

JOHN DOLL
*Acting Director of the United States Patent and Trademark Office*